United States Patent [19]

Yeung et al.

[11] 4,455,089
[45] Jun. 19, 1984

[54] REFRACTIVE INDEX AND ABSORPTION DETECTOR FOR LIQUID CHROMATOGRAPHY BASED ON FABRY-PEROT INTERFEROMETRY

[75] Inventors: Edward S. Yeung; Steven D. Woodruff, both of Ames, Iowa

[73] Assignee: Iowa State University Research Foundation, Inc., Ames, Iowa

[21] Appl. No.: 460,467

[22] Filed: Jan. 24, 1983

Related U.S. Application Data

[63] Continuation-in-part of Ser. No. 411,472, Aug. 25, 1982, abandoned.

[51] Int. Cl.³ .............................................. G01B 9/02
[52] U.S. Cl. ................................. 356/352; 356/246; 356/361
[58] Field of Search ...................... 356/352, 361, 246; 73/61.1 C

[56] References Cited

U.S. PATENT DOCUMENTS

| | | | |
|---|---|---|---|
| 3,619,063 | 11/1971 | Nancy et al. | |
| 4,054,384 | 10/1977 | Hawes | |
| 4,077,719 | 3/1978 | Barrett et al. | |
| 4,170,416 | 10/1979 | Fencil | |
| 4,173,442 | 11/1979 | Snyder | |
| 4,195,931 | 4/1980 | Hara | |
| 4,229,105 | 10/1980 | Silverbage | 356/361 X |

OTHER PUBLICATIONS

Burleigh Instruments, Inc., "Tech Memo for Fabry-Perot Interferometry", No. FP140475, rev. 4/76.
Kadymov, "Fabry-Perot Laser Interferometer for Measuring Plasma Density in Unsteady Flow", *Laser & Unconv. Opt. J.*, (Sweden), No. 64, pp. 16–20, 1976.
Adams, "A Digitized Laser Interferometer . . .", *Can. J. Spectro.*, vol. 21, No. 2, pp. 40–45, Apr. 1976.

*Primary Examiner*—William L. Sikes
*Assistant Examiner*—Matthew W. Koren
*Attorney, Agent, or Firm*—Zarley, McKee, Thomte, Voorhees & Sease

[57] ABSTRACT

A refractive index and absorption detector for liquid chromatography. It is based in part on a Fabry-Perot interferometer and is used for the improved detection of refractive index and absorption. It includes a Fabry-Perot interferometer having a normally fixed first partially reflecting mirror and a movable second partially reflecting mirror. A chromatographic flow-cell is positioned between the mirrors along the optical axis of a monochromatic laser beam passing through the interferometer. A means for deriving information about the interference fringes coming out of the interferometer is used with a mini-computer to compute the refractive index of the specimen injected into the flow cell. The minicomputer continuously scans the interferometer for continuous refractive index readings and outputs the continuous results of the scans on a chart recorder. The absorption of the specimen can concurrently be scanned by including a second optical path for an excitation laser which will not interfere with the first laser, but will affect the specimen so that absorption properties can be detected. By first scanning for the refractive index of the specimen, and then immediately adding the excitation laser and subsequently scanning for the refractive index again, the absorption of the specimen can be computed and recorded.

23 Claims, 10 Drawing Figures

REFRACTIVE INDEX AND ABSORPTION DETECTOR FOR LIQUID CHROMATOGRAPHY BASED ON FABRY-PEROT INTERFEROMETRY

GRANT REFERENCE

This invention was conceived and reduced to practice in part under a grant from the Department of Energy under Contract No. W-7405-eng-82.

RELATIONSHIP TO PRIOR APPLICATION

This is a continuation-in-part application of Ser. No. 411,472, filed Aug. 25, 1982 now abandoned.

BACKGROUND OF THE INVENTION

With the increasing interest in environmental, clinical and other biological problems, there is a growing need for trace analytical methods that are suitable for complex organic mixtures. While gas chromatography, particularly in combination with mass spectrometers, has been successfully applied to the volatile species, high-performance liquid chromatography (HPLC) is many times used for the non-volatile components. Although HPLC technology has made big gains recently, the overall separatory power is still not competitive with gas chromatography. Therefore, there is a real need for improved HPLC detectors, since small sample sizes are required for the highly efficient HPLC separations. Thus, the detectors could be improved with respect to their detectabilities.

Of the three most commonly used HPLC detectors, the fluorometric detectors has been developed sufficiently to be suitable for most situations. For non-fluorescing samples, the absorption detector must be used, but the detection of small differences in two large signals limits conventional detectors to the $10^{-3}$ to $10^{-4}$ range in absorbence. When the species of concern does not show convenient absorption bands, e.g., saturated organic compounds, the refractive index detector is commonly used, despite its poor sensitivity. Since the scope of application of HPLC is virtually related to the detectability of the detectors, there is a real need to improve the refractive index and absorption detectors in sensitivity and detectability.

Absorption detectors can be improved by monitoring an associated effect other than the decrease in light intensity. The most convenient associated effect is the generation of heat through relaxation of the excited molecules of the specimen. The non-uniform heating resulting from absorption of a laser beam gives rise to thermal lens calorimetry. If instead, the temperature gradient, and thus a refractive index (RI) gradient, that is developed is used to deflect a probe laser beam, the technique of photothermal deflection is created. One can also use the heat waves that are generated by a pulsed or chopped excitation source as the basis for photoacoustic detection. These concepts have already been demonstrated as a detection scheme for HPLC. Since the magnitudes of all of these associated effects increase with the power of the excitation (absorbed) light source, one can achieve lower detectabilities by using these associated effects as compared to conventional measurements.

Perhaps the most sensitive way to monitor small changes in the refractive index is interferometry. The same technology that allows one to achieve high frequency stability in lasers and to measure these frequencies to great precision and accuracy, can be applied to the detection of refractive index changes.

One method of doing so would be to use a Mach-Zender interferometer and a single frequency laser to monitor the phase delays in a sample due to absorption and the subsequent heating to detect trace gases. This type of phase-fluctuation heterodyne spectroscopy has been shown to be a fairly good gas chromatography detector. However, detectability depends upon the quality of the interference that can be achieved. The Mach-Zender interferometer has relatively low finesse because a low reflectability mirror (50%) is used for splitting the beam into two paths. It also suffers from having an "idle" arm that can be perturbed by acoustic waves unless the system is evacuated.

Further, arrangement of the optical components is such that system rigidity is difficult to maintain. The Fabry-Perot interferometer, on the other hand, typically has very high finesse, has no "idle" optical paths, and is commercially available with excellent rigidity using materials with low co-efficients of thermal expansion such as Super-Invar, a special composition made principally of nickel and iron and available from such companies as Guterl of Lockport, N.Y.

Additionally, detectability of traditional absorption detectors in HPLC needs improvement. Traditional absorption measurements gain linearly with increasing interaction length. In interferometry, increased length increases the absorbed amount, but at the same time, more volume must be heated up. Therefore, there is no net gain in the accuracy of the change in refractive index. However, the resolution of the interferometer generally increases with the distance between its mirrors, so that longer light paths are still desirable.

Therefore, it is an object of this invention to provide a refractive index and absorption detector which successfully adapts Fabry-Perot interferometry to high performance liquid chromatography detection in a system that allows the improved detectabilities of both the refractive index and absorption.

A further object of this invention is to provide a refractive index and absorption detector which provides superior measurements to traditional HPLC detectors.

A further object of this invention is to provide a refractive index and absorption detector which can provide orders-of-magnitude improvement in detectability over commercial HPLC refractive index detectors.

A yet further object of this invention is to provide a refractive index and absorption detector which achieves a detectability orders-of-magnitude better than standard absorption detectors in HPLC.

A further object of this invention is to provide a refractive index and absorption detector which has a very high finesse, has no "idle" optical paths, and is commercially available with excellent rigidity using materials with low co-efficients of expansion.

Another object of this invention is to provide a refractive index and absorption detector which improves the accuracy of both in the same instrument.

A further object of this invention is to provide a refractive index and absorption detector which is economical, durable, accurate and easy to use.

Additional objects, features and advantages of the invention will become apparent with reference to the accompanying specification and drawings.

SUMMARY OF THE INVENTION

This invention utilizes an optical flow-cell positioned between the mirrors of a Fabry-Perot interferometer. A monochrometic laser beam is passed through the interferometer and flow cell to a photoelectric detector which measures the laser light transmitted by the combination. A minicomputer repetitively scans the interferometer and digitizes the analog photoelectric detector signal with an analog to digital converter and stores the information. The minicomputer derives the value of the distance between the interferometer's two mirrors for the maximum constructive interference of the laser beam for each scan of the interferometer and permanently saves that value for later recall and/or converts that value to an analog signal to be output to a chart recorder for a visual record. The chart therefore gives a visual record of the change in refractive index of the sample passing through the flow cell. By using the high finesse of the Fabry-Perot interferometer, accuracy and detectability of changes in refractive index is greatly improved.

In another embodiment of the invention, a second laser, an excitation light source, is directed to the flow cell so that the sample is "excited" by the excitation laser. The difference between the refractive index measurement taken preceding the introduction of the excitation laser compared to the refractive index reading after excitation, allows the absorption of the sample to be computed and displayed on the chart recorder. Again, by utilizing the Fabry-Perot interferometer with the flow cell, and the excitation laser, detectability measurements are greatly improved over the conventional absorption detectors.

DETAILED DESCRIPTION OF THE PREFERRED EMBODIMENT

Figure 10:
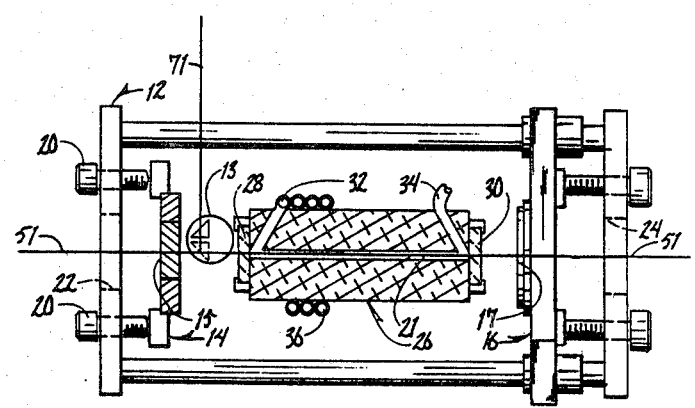
FIG. 10 is a side view of a refractive index and absorption detector for liquid chromatography with a sectional view of the single channel flow cell taken along lines 10—10 of FIG. 1.

In reference to the drawings, and particularly FIG. 10, there is shown a refractive index and absorption detector for liquid chromatography based on Fabry-Perot interferometry in accordance with the invention.

A Fabry-Perot interferometer 12 with mirrors 15 and 17 having a flatness of greater than $\lambda/40$ and a reflectivity of greater than 0.9 is used having a mechanically adjustable mirror assembly 14 and a piezoelectrically driven moveable mirror assembly 16 which can be driven electrically along the longitudinal axis of the interferometer frame 18. A light path is provided by openings 22 and 24 and by the partially transmitting mirrors 15 and 17 and by the cell windows 28 and 30 and the cell bore 21 all of which are aligned along an axis parallel to the longitudinal axis of the Fabry-Perot interferometer. By minute adjustments of the non-driven mirror assembly 14 via the adjustment controls 20 a monochromatic light source traversing the light path will exit the system only when the distance between the mirrors 15 and 17 is equal to the wavelength of the incident monochromatic light, or to an integral multiple of said wavelength so that constructive interference of the light takes place.

Figure 1:
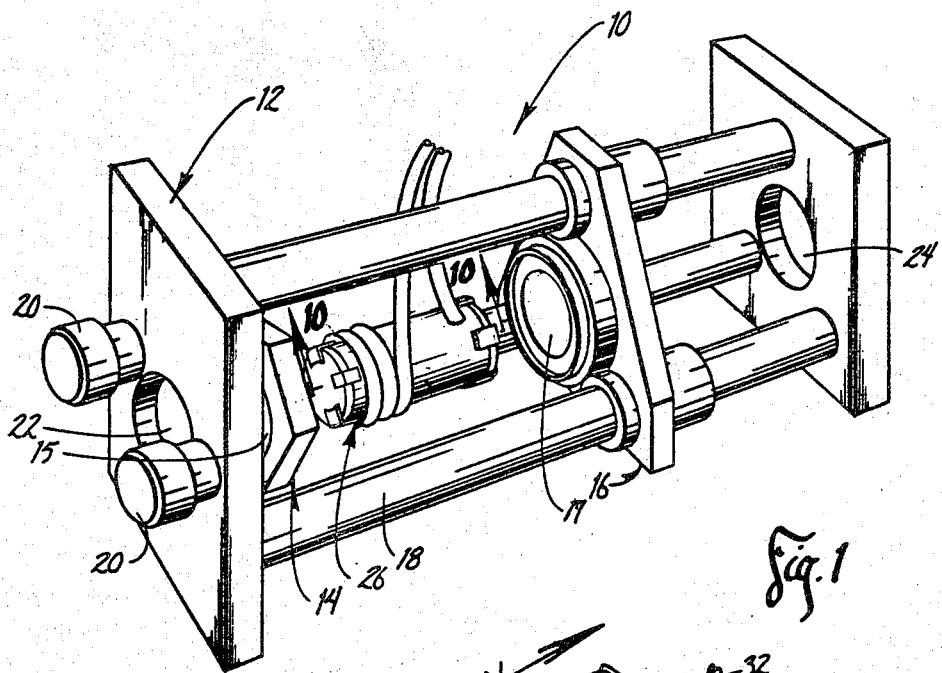
FIG. 1 is a perspective view of the Fabry-Perot interferometer and a single channel chromatographic flow-cell.

A chromatographic flow cell 26 (See FIG. 10) or alternate cell embodiments 25 and 27 (See FIGS. 2, 3 and 9) is positioned along an optical light path of the interferometer between mirrors 15 and 17 by a metal rod (not shown) attached to the cell and to metal plate (not shown) supporting the interferometer. By reference to FIGS. 1 and 10, it can be seen that flow cell 26 comprises a cylinder having antireflection coated windows 28 and 30 sealingly mounted over opposite ends covering the sample bore 21. Additionally, a specimen inlet tube 32 and a specimen outlet tube 34 provide a means for introducing the specimen into the flow-cell and for removing it during operation. The thermally contacted coils 36 of inlet tube 32 enable the incoming specimen to reach an approximate equilibrium temperature with the flow cell 26. An alternate cell embodiment 25 (See FIGS. 2 and 3) has in addition a second bore 40 parallel to the first bore 21 and spaced an arbitrary distance from it and covered by the windows 28 and 30. The second bore 40 also has separate specimen inlet tube 42 and outlet tube 44 to provide a means for introducing and removing the specimen during operation and may have thermally contacted coils (not shown) similar to coils 36. An alternate cell embodiment 27 (See FIG. 9) comprises a cylinder with the ends cut to enable windows to be mounted at Brewster's angle with respect to the incident light beam and a bore 33 drilled at an angle to the windows such that the light beam deflected by the refraction through the windows and the specimen solvent can traverse the center of the bore from one window to the other. A second bore 33a intersecting the first is oriented to allow a second light beam entering the cell perpendicular to the window 35 and will exit window 31 at Brewster's angle and intersect the light beam traversing the bore 33 such that the reflection of the second light beam will be colinear with the first light beam along the bore 33. Specimen inlet tube 37 and outlet tube 39 provide a means for introducing and removing the specimen during operation.

Figures 2, 3:
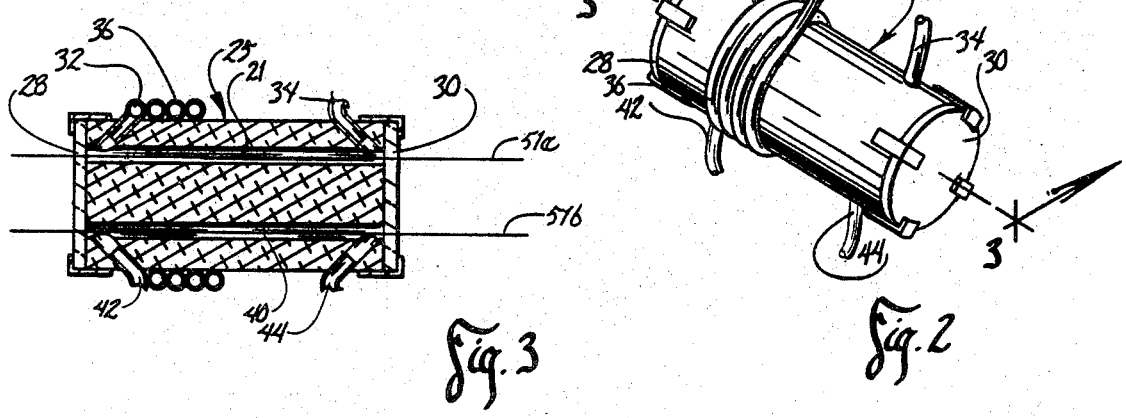
FIG. 2 is a perspective view of a double channel chromatographic flow cell in accordance with the invention.
FIG. 3 is a sectional view taken along lines 3—3 of FIG. 2.
Figure 9:
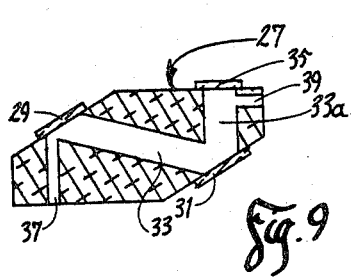
FIG. 9 is a sectional view of an alternative embodiment of the flow cell.
Figure 5:
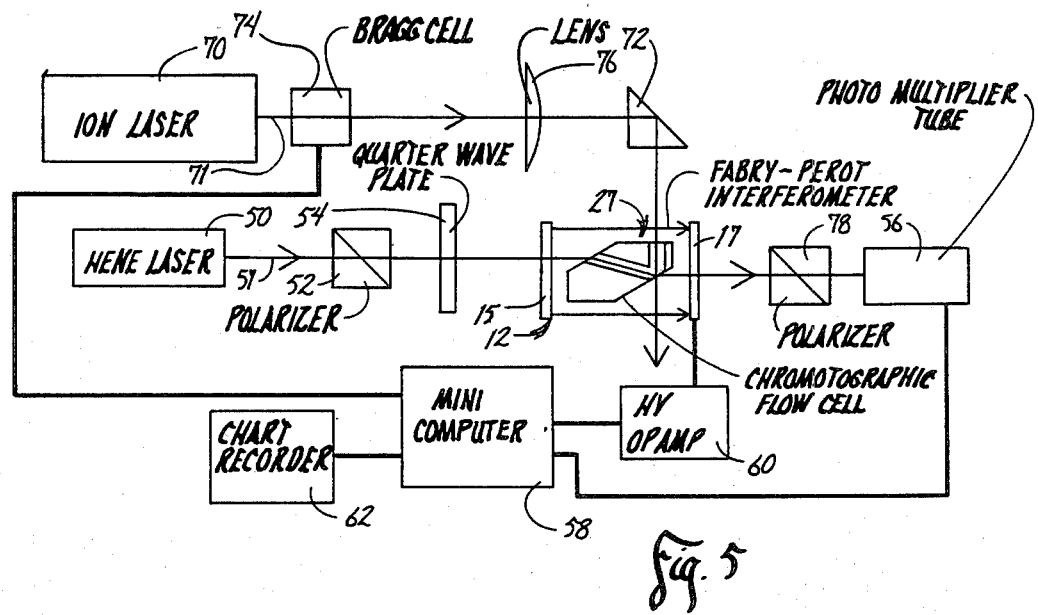
FIG. 5 is a schematic of a combined refractive index and absorption detector in accordance with the invention.
Figure 4:
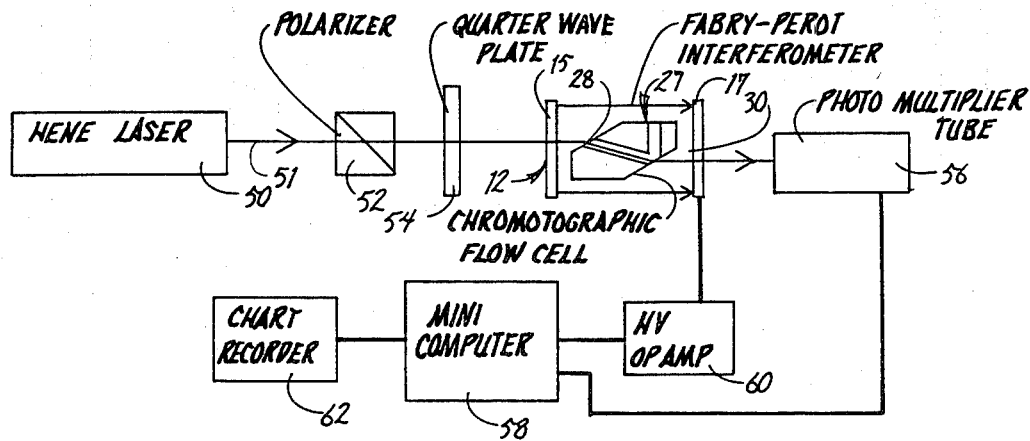
FIG. 4 is a schematic of an alternative embodiment of a refractive index detector in accordance with the invention.

The total working combination of the invention can be seen in FIGS. 4 and 5 in conjunction with the cell embodiment in FIG. 9. Flow cell 26 of FIGS. 1 and 10 can be used with the combination of FIGS. 4 and 5. Flow cell 25 of FIGS. 2 and 3 can be used with the combination of FIG. 4. For the detection of the refractive index of a specimen, a single frequency, monochromatic laser of known wavelength is preferred for use with the system. However, a stable laser with well defined longitudinal modes may be used. In one suitable embodiment (FIG. 4), a single-frequency helium-neon (HeNe) laser 50 can be used to provide a monochromatic light beam 51 with a frequency stability of ±1 MHz per second, or ±3 MHz per minute, or ±10 MHz per hour. To avoid feedback into the stabilization mechanism of the laser 50, in the single beam mode, a prism polarizer 52, for example a Glan-Thompson polarizer, is placed in the polarization orientation of the laser beam 51 followed by a quarter-wave plate 54, the combination of which rejects retroreflected light before it can reenter the laser cavity. The interferometer 12 can be a Tropel, Model CL-100 with λ/50, 98 percent reflectivity mirrors.

The chromatographic flow cell 27 can be machined to fit inside the interferometer 12. It can be made out of a 1.3 centimeter diameter, 2.5 centimeter long aluminum rod with a specimen bore 33 1.0 centimeter long and 0.32 centimeter inside diameter having a sample volume of about 80 microliters. Flow cell 27 can be machined to be an integral part of one of the interferometer mirror mounts. Windows 29 and 31 are 0.25 inch square sections of microscope slides and are held sealingly in place by epoxy glue.

In the use of the invention using the cell embodiment in FIG. 9 and a Fabry-Perot interferometer, such as the Tropel Model CL-100, as portrayed schematically in FIG. 4, the laser beam 51 is aligned to pass through the interferometer 12 and the cell 27 and the interferometer is adjusted for maximum finesse with eluent in the cell 27 by observing the laser light passing through the interferometer photoelectrically on an oscilloscope (not shown) while continuously scanning the interferometer electrically. The interferometer 12 is then scanned on command by the minicomputer 58 which sends an analog signal to the high voltage operational amplifier 60 which applies the signal amplified to a much greater voltage to the interferometer's pizoelectric driver. The signal from the photomultiplier tube 56 is sent to the minicomputer 58 and digitized by an analog to digital converter and recorded on command by the computer 58. In operation, the computer 58 generates an analog voltage ramp signal composed of 2048 incremental voltage steps to be sent to the amplifier 60 and then to the interferometer 12 to step-wise scan the interferometer. For each step in the voltage ramp, the minicomputer 58 digitizes the signal from the photomultiplier 56 and saves the digital value in its memory. Upon completion of the voltage ramp the minicomputer 58 returns the voltage to its value at the beginning of the ramp and computes the position of the interferometer mirror 14 which gave the maximum throughput of the laser beam 51.

In the use of the invention using the cell embodiment 26 in FIG. 10 and the Fabry-Perot interferometer, such as Burleigh Model RC-110, the laser beam 51 is aligned to pass through the interferometer 12 and the cell 26. The interferometer is adjusted as before for maximum finesse with eluent in the cell 26 and the cell is aligned to the laser beam 51 such that the beam does not reflect off the wall of the cell bore 21. The interferometer is scanned by the computer 58 and the data collected as described previously.

In the use of the invention using the cell embodiment 25 in FIG. 3 and the Burleigh Model RC-110 interferometer, the laser is first passed through a ⅛ inch thick glass flat at an approximately 45° angle with the laser polarization perpendicular to the plane of incidence and reflection. As a result, the laser beam 51 is reflected off the front and back surfaces of the glass flat to provide two parallel beams approximately 3/16 inch apart and adjustable by changing the angle of incidence of the laser beam 51. The spacing between the two beams is adjusted to have each beam pass through one of the two bores in the cell 26 simultaneously without reflecting off the wall of the cell bores. The laser beams 51a and 51b are then aligned to pass through the interferometer 12 and the cell 25. Each beam is then directed with mirrors to separate photomultipliers. The interferometer is adjusted as before for maximum finesse with eluent in both bores of the cell 25 except that both beams are monitored simultaneously on an oscilloscope and the best compromise of optimum finesse in each beam is determined as the correct adjustment. The interferometer is scanned by the computer 58 and the data collected as described previously, except that both phototubes (not shown) are monitored and digitized and the data is saved in separate arrays and the peak position is determined for each array. Also in this configuration the polarizer 52 and the quarter wave plate 54 can be eliminated since the return reflection from the interferometer off the glass flat to the laser is only one per cent of the original incident intensity and no longer interferes with the laser stabilization.

FIGS. 5, 9 and 10 illustrate the components of the invention for accurately detecting the absorption of a specimen in two possible configurations. In FIG. 5, the alternate cell 27 of FIG. 9 is employed. The basic structure of FIG. 4 is retained with the following modifications. A c.w. (constant wave) laser such as a Control Laser Model 554 argon ion laser operating at 514.5 nanometers emits laser beam 71 to excite the molecules of the specimen. The laser beam 71 is passed through an optical shutter such as a Coherent Modulator Division Model 304 Bragg cell to enable computer controlled transmission of light pulses of well defined total energies from the continuous wave laser beam 71. A long focal length lens 76 serves to reduce the diameter of laser beam 71 at the cell 27 to match the diameter of laser beam 51 such that they will be coincident inside the cell. Lens 76 in one embodiment can be a 50 centimeter focal length lens. The laser beam 71 is directed to flow cell 27 by light beam steering optics such as a right angle prism 72.

The chromatographic flow cell 27 includes a second optical path for the excitation laser beam 51. Introduction into the optical path of interferometer 12 is achieved by using excitation laser beam 51 at a polarization direction perpendicular to the incident plane of the laser beam 71 on the Brewster window 31 to take advantage of the natural reflection of the cell window 31. About 15% of the incident intensity is thus introduced. Laser beam 51 is not maintained after two or three passes in the interferometer cavity because of the unfavorable losses at windows 29 and 31 for this polarization direction. To reject any part of laser beam 71 which does exit the interferometer 12 in the direction of the photomultiplier tube 56, a second polarizer 78 is inserted into the optical path between interferometer 12 and photomultiplier tube 56 and oriented to reject any light with the same polarization as laser beam 71. The laser beam 51 is polarized by the Brewster windows 29 and 31 orthoganal to the direction of polarization of laser beam 71 from laser beam 51's original circular polarization induced by the quarter wave plate 54.

In the use of the invention using the alternate cell embodiment 27 the invention works as follows. The computer 58 generates a linear voltage ramp comprised of 2048 steps with a digital to analog converter which is amplified to a much higher voltage by the high voltage operational amplifier 60 to drive the interferometer 12. The computer digitizes the voltage signal from the photomultiplier tube 56 with an analog to digital converter at each of the 2048 steps and stores each of the values in an array in memory. Upon completion of the voltage ramp the minicomputer 58 returns the voltage to its value at the beginning of the ramp. The computer then switches on the Bragg cell 74 for a specified period of time to transmit a specific amount of laser light energy to the cell 27. After the Bragg cell 74 is switched off by the computer, the computer pauses for a specified period of time to allow the eluent and specimen to thermally relax and then the computer repeats the scan and data collection sequence. The position of the interferometer mirror for which there was maximum laser light transmission is then calculated for each array (or scan) and the difference in the two calculated positions is a linear measure of how much light energy was absorbed by the eluent and specimen in the cell 27. The difference value is then stored in memory and also output from the computer by a digital to analog converter to a chart recorder 62 for an immediate record of the event. The computer then waits for a specified period of time and repeats the whole process for the next data point. The collection of data points which make up the chromatogram are stored on a permanent memory storage device to be recalled later.

In FIG. 10, the alternate cell 26 is shown in an embodiment which could be used to measure either refractive index or absorption. Its use in measuring refractive index has been described and now its use in measuring absorption of light will be described. In addition to the cell 26 which is aligned as previously described, a small right angle prism 13 mounted on a rod which can be rotated by a stepping motor under computer control is positioned between the cell 26 and one of the mirrors 15 such that the prism can be rotated into a position which will steer a laser beam 71 into the cell bore 21 and along the axis of the probe laser beam 51.

In the use of the invention using the alternate embodiment 26 in FIG. 10 the invention works as follows. The computer 58 generates the scan and data collection sequence described earlier. The computer then rotates the prism 13 into position to steer the excitation laser beam 71 down the cell bore 21. The computer waits a specified period of time for vibrations from the stepping motor to decay and then switches on the Bragg cell 74 for a specified period of time to transmit a specific amount of laser light energy to the cell 26. The prism 13 is rotated by the computer out of the optical path of probe laser 51 immediately after the Bragg cell 74 is switched off and after a specified delay period to allow the eluent and specimen to thermally relax, the scan and data collection sequence is repeated. The mirror positions for maximum light transmission for the two scans are determined as described previously and the difference stored in permanent memory and also output as an analog signal to a chart recorder for an immediate record. The computer then waits a specified period of time and then repeats the sequence to get another data point.

In operation, the invention works as follows: To produce a chart record of refractive index of a specimen, a linear ramp is generated by a digital-to-analog converter (DAC) associated with minicomputer 58 and is amplified by high voltage operational amplifier 60 to scan interferometer 12 by operation of piezoelectric crystal drivers (not shown). The digitization and storage of the output of photomultiplier tube or tubes 56 is accomplished by an analog-to-digital converter (ADC) for each step in the ramp. After each complete scan, which takes less than 0.3 seconds, the computer derives the value of the distance between mirrors 15 and 17 of interferometer 12 which produces maximum constructive interference by deciding where along the ramp the maximum photomultiplier tube 56 output occurs. After digital-to-analog conversion, this value is displayed on chart recorder 62. In practice, the gain of the operational amplifier 60 is adjusted so that a complete ramp corresponds to one free spectral range or more for the interferometer 12. The computer monitors the interference peak and keeps track of it when two or more peaks are present, or the tracked peak is out of range. There is a corresponding reset on the chart display (See FIG. 8) which degrades the aesthetic value of the display, but does not affect the usefulness of the measurement. When such a reset occurs, computer 58 simply adds one free spectral range to the peak position and continues monitoring. In fact, allowing resets and accounting for these properly in principle provides an unlimited dynamic range for the measurement in change in refractive index without adjusting the interferometer.

Figure 6:
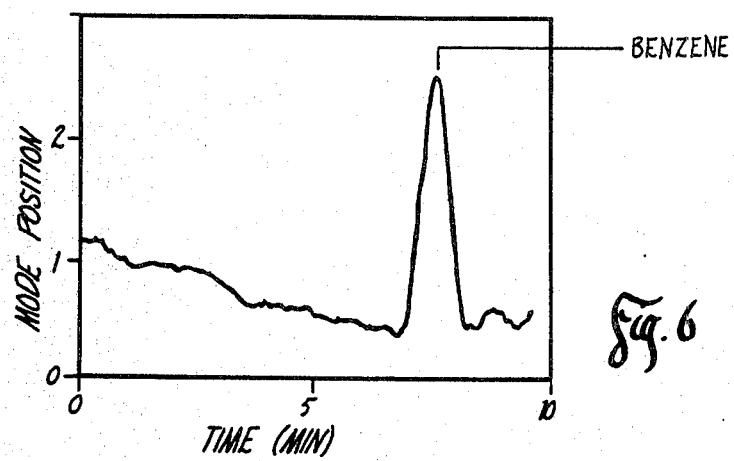
FIG. 6 is a chart recorder record for a refractive index chromatogram.

FIG. 6 shows a chromatogram of a specimen prepared in this manner, with the ordinate being the position of a particular interferometric peak as determined by minicomputer 58. The chart recorder 62 output was refreshed by the minicomputer 58 at 0.3 second intervals, and no time constant was introduced at the output. The main peak (benzene) corresponds to a refractive index difference of $3 \times 10^{-7}$, as determined from the differences in refractive index for benzene ($N_D = 1.5011$) and for acetonitrile ($n_C = 1.3442$) and the dilution factor from the sample loop size and the volume of the whole benzene peak. The "bump" after the benzene peak corresponds to an unidentified contaminant. Also injected was a sample of a 1:10 dilution of the previous sample using a five second time constant generated digitally by the computer. It is estimated the signal to noise ratio of the peak of the change in refractive index of $3 \times 10^8$ to be 6. This implies a detectability of refractive index changes of $1.5 \times 10^{-8}$ (S/N=3), which is roughly an order-of-magnitude better than those of commercial refractive index detectors. When using the double beam mode of cell 25, the detectability of refractive index changes was found to be yet another order-of-magnitude better.

In its absorption detector mode, operation is accomplished as follows: The computer 58 generated a ramp and stores the interferometric scan as described above. The Bragg cell 74 is then turned on under computer control for a period of time, typically one second. While waiting the computer 58 determines the location of the peak for the scan before irradiation. Immediately after irradiation, a second scan is taken to determine the shift of the peak due to absorption. The difference in peak locations is then stored and plotted as the absorption chromatogram. To insure that thermal relaxation of the system is complete between data points, the data gathering cycle is repeated once every 15 seconds, but is dependent upon the cell configuration and experimental conditions. This system therefore simultaneously provides a refractive index chromatogram and an absorption chromatogram.

Figure 7:
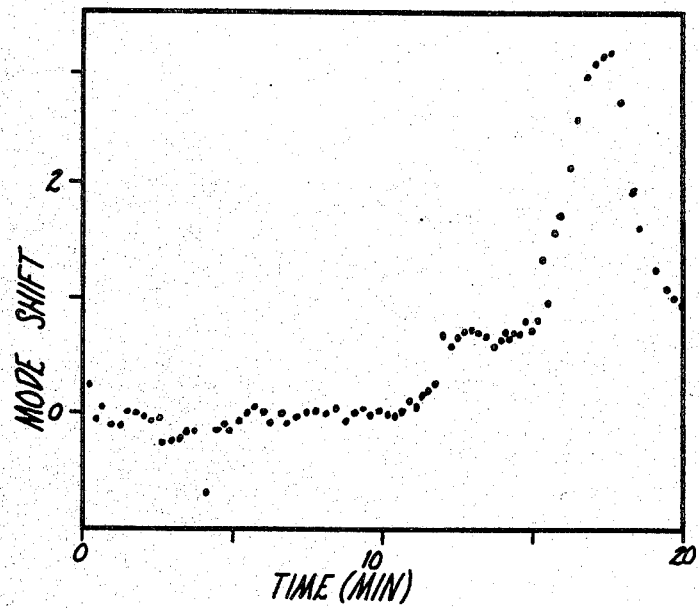
FIG. 7 is a chart recorder record for an absorption chromatogram.

FIG. 7 shows the chart of an absorption chromatogram. The ordinate represents the differences in the interferometric peak positions before and after each irradiation of the ion laser 70 pulse. This quantity is found to be proportional to the absorbance over the range of $2.6 \times 10^{-6}$ to $2.6 \times 10^{-4}$ using five standard solutions. Data points are gathered at 15 second intervals, so the chromatogram, without any smoothing, shows up as individual points. The main chromatographic peak then represents an absorbance of no greater than $2.6 \times 10^{-5}$. Except for three stray points, the average noise is about 1/30 of the peak height, implying a detectability of $2.6 \times 10^{-6}$ absorbance units (S/N=3), or about two orders-of-magnitude better than commercial units. Further enhancements can be expected using higher powered lasers.

Figure 8:
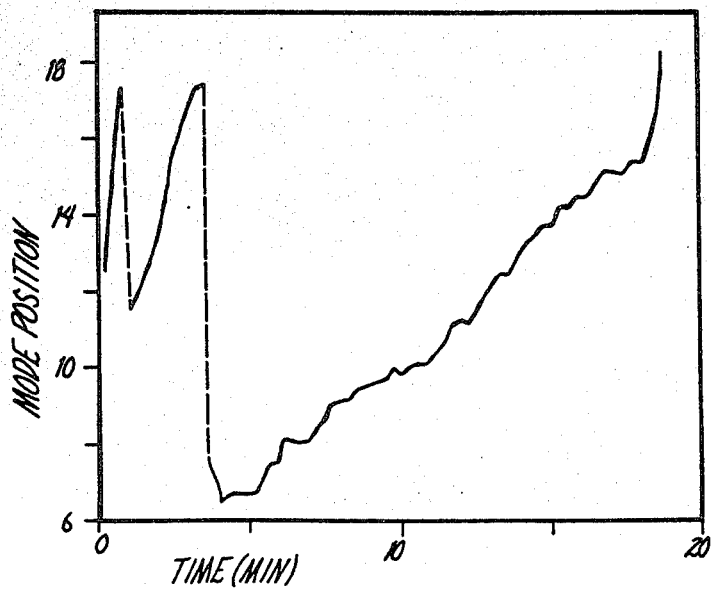
FIG. 8 is a refractive index chromatogram for FIG. 7.

To show that FIG. 7 is not an artifact of changing refractive index in the absence of absorptions, FIG. 8 was simultaneously obtained by recording the interferometric peak positions before each exciting laser pulse, but after the effects of previous pulse has decayed. The "resetting" of the interferometric scan is shown as the dashed lines, as discussed above. Thus, the present system is suitable for simultaneous monitoring of refractive index and absorption.

As mentioned earlier from time to time, three different cell embodiments 25, 26 and 27 (See FIGS. 3, 10 and 9) have been shown. The cells 25 and 26 of FIGS. 10 and 3 have been earlier described in detail. The cell 27 of FIG. 9 is suitable for use in a single beam mode (See FIG. 4). The cell windows 29 and 31 are oriented Brewster's angle to the incident laser beam to eliminate the need for anti-reflective coating. The bore 33 is oriented to pass the deflected laser beam when it enters the eluent. Alternatively, cell 27 can be used in a two-beam mode (See FIG. 5) utilizing an excitation beam 71 and a probe beam 51. The window 35 admits the excitation laser beam 71 and passes it down bore 33a to be reflected off window 31. Bores 37 and 39 are inlets and outlets, for eluent and specimen, respectively.

Thus, the invention achieves at least all of its stated objectives. It is to be understood that changes can be made in the embodiments herein described while staying within the boundaries of the invention.

What is claimed is:

1. A refractive index and absorption detector for liquid chromatography utilizing a Fabry-Perot interferometer and a chromatographic flow cell comprising:
   (a) a Fabry-Perot interferometer having a framework to which are attached first and second adjustable mirrors perpendicularly to and in alignment with a beam path passing through said framework, said second mirror being movable along said beam path;
   (b) a chromatographic flow cell positioned in operative alignment between said first and second mirrors and having at least one bore extending therethrough, each said bore having a separate inlet and outlet for introduction of liquids into said bore, and windows sealingly placed over opposite ends of each said bore to contain said liquids, and to allow a light beam from a light source to enter and exit each said bore; and
   (c) means to detect the interference fringes produced by said interferometer.

2. The device of claim 1 wherein said windows are perpendicular to said beam path.

3. The device of claim 2 wherein said flow cell has one bore for reception of a light beam from a light source.

4. The device of claim 2 wherein said flow cell has two parallel bores namely, a probe bore and a monitor bore, each with separate inlets and separate outlets said probe bore being oriented so as to receive a probe light beam from a probe light source, said monitor bore being oriented to receive a monitor beam from a monitor light source.

5. The device of claim 4 wherein each said inlet and outlet pair are in fluid communication with a specimen fluid for continuous circulation of said fluid through each of said bores.

6. The device of claim 5 wherein said inlet to said probe bore is attached in fluid communication to a tube means which is in turn in fluid communication with a fluid reservoir and which is circumferentially wrapped around said flow cell a plurality of turns and thermally contacted with said flow cell so that when said fluid circulates through said tube means into said inlet of said probe bore, said flow cell is in thermal equilibrium with said fluid.

7. The device of claim 1 wherein said windows are oriented at Brewster's angle with respect to said beam path and said probe bore is canted parallel from said beam path to accomodate the angular refraction of light occasioned by said windows oriented at Brewster's angle.

8. The device of claim 7 wherein said flow cell includes an excitation bore which is essentially oblique to said bore and co-terminates with said bore at an exit end of said bore, said excitation bore having an entrance end covered by a window which is perpendicular to said excitation bore through which enters an excitation light beam from an excitation light source, said exit end of said excitation bore co-terminating at said exit end of said bore.

9. The device of claim 8 wherein said excitation light source comprises a laser beam source for exciting the molecular structure of a specimen and is placed in operative alignment along said beam path.

10. The device of claim 9 wherein said excitation light source comprises an argon ion laser.

11. The device of claim 8 wherein said excitation beam is at a polarization direction perpendicular to said light beam.

12. The device of claim 1 wherein said light source comprises a means for providing a laser beam having well defined longitudinal modes.

13. The device of claim 12 wherein said means for providing a laser beam having well-defined longitudinal modes is oriented so that said laser beam follows said beam path through said bore.

14. The device of claim 13 wherein said laser beam is a helium neon laser.

15. The device of claim 1 wherein a means to detect interference fringes produced by said interferometer is placed along said beam path behind said flow cell and interferometer.

16. The device of claim 15 wherein said means to detect interference fringes is a photomultiplier tube.

17. The device of claim 16 wherein said means for electrically detecting interference fringes includes an interferometer filter to reject room light placed in said beam path.

18. The device of claim 1 wherein said means for detecting interference fringes comprises:

an interference filter positioned along said beam path and receiving said probe beam from said interferometer;

a photomultiplier tube receiving said probe beam from said interference filter;

means for generating a linear voltage ramp to scan said interferometer;

means for digitizing the output of said photomultiplier tube and storing said output in a memory;

means for determining the value of the distance between said normally fixed mirror and said movable mirror for maximum constructive interference, by detecting maximum phototube output along said linear voltage ramp;

means for displaying the value.

19. The device of claim 1 wherein said means for electrically detecting interference fringes comprises:

a minicomputer which generates a linear voltage ramp, which is amplified by a high-voltage operational amplifier to scan said interferometer;

said minicomputer digitizing the output of said photomultiplier tube for each step in the ramp and storing said output in computer memory, after each ramp scan said minicomputer determines where the maximum photo-tube output occurs, which correlates with the value of the distance between said fixed mirror and said movable mirror for maximum constructive interference to occur;

a digital-to-analog converter to convert said distance value to an analog signal.

19.

20. The device of claim 19 wherein said excitation beam is deflected passing through a Bragg cell to produce light pulses of well-defined total energies.

21. The device of claim 19 wherein said excitation beam passes through a lens which focuses said excitation beam to match the size of said probe beam.

22. The method of detecting refractive index and absorption by utilizing liquid chromatography in association with a Fabry-Perot interferometer, comprising the following steps:

placing a chromatographic flow cell along the optical path of a Fabry-Perot interferometer;

directing a monochromatic laser beam along the optical path of said interferometer;

detecting the intensity changes from said interferometer;

generating a linear ramp to scan said interferometer;

digitizing the output of said detector and storing said digitizations;

determining maximum probe laser throughput along said ramp;

converting said digitization maximum values to analog signals; displaying said analog signal on a chart recorder.

23. The method of claim 22 further comprising the following steps:

introducing an excitation laser along a second optical path into said flow cell so that said first optical path and second optical path are in fluid communication with one another;

operating said probe laser and recording this output on said chart recorder;

operating said excitation laser immediately thereafter and recording the output on said chart recorder.

* * * * *